US006328957B1

(12) United States Patent
Colston et al.

(10) Patent No.: US 6,328,957 B1
(45) Date of Patent: Dec. 11, 2001

(54) HEAT SHOCK PROTEINS AND THE TREATMENT OF TUMORS

(75) Inventors: Michael J. Colston; Douglas Lowrie; Katalin V. Lukacs, all of London (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 09/225,234

(22) Filed: Jan. 4, 1999

Related U.S. Application Data (63) Continuation of application No. 08/433,475, filed on Jun. 30, 1995, now abandoned.

(30) Foreign Application Priority Data

Nov. 13, 1992 (GB) ................................. 9223816
Nov. 15, 1993 (WO) ................................. PCT/GB93/02339

(51) Int. Cl.[7] .......................... A61K 48/00; C12N 15/88; C12N 15/63
(52) U.S. Cl. ...................... 424/93.2; 514/44; 435/320.1; 435/455; 435/458
(58) Field of Search ................... 514/14, 44; 435/320.1, 435/69.1, 455, 458; 536/23.1

(56) References Cited

U.S. PATENT DOCUMENTS

| 5,328,470 | 7/1994 | Nabel et al. ........................ 601/101 |
| 5,580,859 | 12/1996 | Felgner et al. ........................ 514/44 |
| 5,589,466 | 12/1996 | Felgner et al. ........................ 514/44 |

FOREIGN PATENT DOCUMENTS

| 45036/89 | 5/1990 | (AU) . |
| 29461/92 | 6/1993 | (AU) . |
| 37527/93 | 10/1993 | (AU) . |
| 37665/93 | 10/1993 | (AU) . |
| WO 89/12455 | * 12/1989 | (WO) ............................ A61K/3/02 |
| 90/04604 | 5/1990 | (WO) . |

OTHER PUBLICATIONS

Orkin et al. Report and Recommendations of the Panel to Assess the NIH Investment in Research on Gene Therapy, Dec. 1995.*
Crystal et al. Science. 270: 404–410, 1995.*
Eck et al. Goodman & Gilman's The Pharmacological Basis of Therapeutics. 9th Ed. McGraw–Hill, 1995.*
Knauf et al. FEBS. 309 (3): 297–302, Sep. 1992.*
Schwartz et al. Biochemical and Biophysical Res. Com. 169(3): 941–946, Jun. 1990.*
Silva et al. Microb. Pathog. 12(1): 27–38, Jan. 1992.*
Hug et al. Biochimica et Biophysica Acta. 1097(1): 1–17, Jul. 1991.*
Crowley et al. Seminars in Surgical Oncology. 9(3): 273–8. May 1993.*
Launois et al. Scandinavian Journal of Immunology. 38(2): 167–76, Aug. 1993.*
Golumbek et al. Science. 254: 713–716, Nov. 1991.*
Gene Therapy (1997) 4, 346–350 Lukacs et al "In vivo gene therapy of malignant tumours with heat shock protein–65 gene".
Molecular and Cellular Biology, vol. 9, No. 5, May 1989, p. 2279–2283 Jindal et al "Primary Structure of a Human Mitochondrial Protein Homologous to the Bacterial and Plant Chaperonins and to the 65–Kilodalton Mycobacterial Antigen".
Pierce, S.K. (1994) Experimentia 50: 1026–1030, Molecular Chaperones in the Process and Presentation of Antigen . . .
Blood vol. 82, No. 9 (Nov. 1), 1993 pp 2865–2871 Manara et al "New Insights Suggesting a Possible Role of a Heat Shock Protein 70–kD Family–Related Protein in Antigen Processing/Presentation Phenomenon in Humnas".
J. Exp. Med. vol. 178, 10/93 pp 1391–1396 Udono et al "Heat Shock Protein 70–associated Peptides Elicit Specific Cancer Immunity".
Journal of Immunology vol. 147, No. 1 Jul. 1, 1991 pp 312–319 McKenzie et al "Sequence and Immunogenicity of the 70 k–Da Heat Shock Protein of *Mycobacterium leprae*[1]".
Journal of Leukocyte Biology, vol. 0, No. 2, 1991, New York, US p. 68 Lowrie, D. et al (Abstract 194).
Microbial Pathogenesis, vol. 12, No. 1, Jan. 1992, Aberdeen, pp. 27–38, Silva et al.
Proceedings of the National Academy of Science of USA, vol. 83, pp. 3121–3125, Ullrich et al. May 1986.
Immunology Today, vol. 10, No. 7, Jul. 1989, Cambridge GB, pp. 218–221, Watson, J.D. Leprosy: understanding protective immunity.
Journal of Experimental Medicine, vol. 178, Jul. 1993, pp. 343–348, Lukacs, K et al Tumor cells transfected with a Bacterial Heat–Shock Gene Lose . . . .
Lukacs et al The Journal of Immunology, vol. 143, 3731–3736 No. 11 Dec. 1989 "MHC Unrestricted Transfer of Antilisterial Immunity by Freshly Isolated Immune CD8 Spleen Cells".

* cited by examiner

Primary Examiner—Dave T. Nguyen
(74) Attorney, Agent, or Firm—Nixon & Vanderhye P.C.

(57) ABSTRACT

An expression vector is provided for use in the treatment of neoplasms which vector comprises nucleic acid including at least one which encodes in expressible form a polypeptide which is a heat shock polypeptide (hsp) or a chaperone.

15 Claims, 7 Drawing Sheets

GROWTH OF TUMOURS IN MICE

GROWTH OF TUMOURS IN MICE

EXPRESSION OF P53 IN hsp65 - TRANSFECTED CELLS

Fig. 5

HEAT SHOCK PROTEINS AND THE TREATMENT OF TUMORS

This application is a continuation of application Ser. No. 08/433,475, filed Jun. 30, 1995, now abandoned, incorporated by reference.

The invention relates to expression vectors which express heat shock proteins or chaperones.

Conventionally, solid tumours are treated by a combination of surgery, chemotherapy and radiotherapy. Other neoplasms, such as leukaemia, are also treated by chemotherapy and radiotherapy. However, these methods of treatment are not ideal because radiotherapy and chemotherapy cause unpleasant side effects and some solid neoplasms, such as brain tumours, cannot be treated surgically. For these reasons new methods for treating and preventing tumours are constantly being sought. One method which is currently being investigated is the use of gene transfer of, for example, IL-2 or TNF encoding genes.

Tumours may be induced in mice by administering tumour cell lines. In particular, mice to which the murine macrophage tumour cell line J774 is administered develop large, intraabdominal, highly malignant lymphoreticular neoplasms. Surprisingly, it has been found that, when such tumour cells are transfected with the gene encoding the *Mycobacterium leprae* 65 kD hsp and subsequently administered to mice, there is a decrease in or loss of tumourigenicity of the cells. Furthermore, when such transfected cells are administered to a host, such as a mouse, and the host is subsequently challenged with tumour cells from the same cell line which have not been transfected, no tumour develops. Therefore the technique has potential for an alternative or additional approach to the treatment of neoplasms.

The present invention provides a mammalian cell or an expression vector for use as a therapeutic agent, for example in the treatment of neoplasms comprising nucleic acid including at least one sequence which encodes in expressible form a polypeptide which is a heat shock polypeptide (hsp) or a chaperone.

A polypeptide includes, for example, a heat shock protein, a heat shock protein fragment, a heat shock protein analogue, a chaperone, a chaperone fragment or a chaperone analogue. A fragment will be at least 10, preferably at least 15, for example, 20, 25, 30, 40, 50 or 60 amino acid residues in length. An analogue will be generally at least 70%, preferably at least 80% or 90% and more preferably at least 95% homologous to the heat shock protein or chaperone over a region of at least 5, preferably at least 10, for example 20, 40, 60 or 100 or more contiguous amino acids. The amino acid sequence of an analogue may differ from that of the heat shock protein or chaperone when at least one residue is deleted, inserted or substituted.

A chaperone is a protein which mediates the folding of proteins into their active conformation. Polypeptides exist which are both chaperones and heat shock polypeptides. Heat shock polypeptides, such as hsp60, hsp65 and hsp70 are involved in the folding and translocation of other proteins, and are therefore also chaperones.

Fragments include polypeptides which are not glycosylated but which retain their anti-neoplasm activity. Analogues include proteins which have been engineered with a different amino acid sequence, but which retain their anti-neoplasm activity.

The nucleic acid of the expression vector of the present invention may be double or single stranded and may be RNA or DNA. Generally the nucleic acid includes only one sequence which encodes a polypeptide as defined herein, but the nucleic acid may include 2, 3, 4 or more sequences which separately encode a polypeptide as defined herein.

The nucleic acid comprised in the expression vector or cell line of the present invention encodes any suitable polypeptide as defined herein but preferably does not encode a polypeptide of the host. Preferably the polypeptide is a chaparonin and most preferably the polypeptide is bacterial hsp, such as Mycobacterium leprae 65 kD hsp or *Mycobacterium leprae* 70 kD hsp.

The expression vector of the invention is generally a virus, plasmid, cosmid, episomal vector or naked nucleic acid. Generally the naked nucleic acid comprises the sequence encoding the polypeptide together with regulatory sequences. The naked nucleic acid generally comprises at least 100, for example at least 200, 400, 600, 800, 1000, 2000 or 4000 base pairs. The naked nucleic acid may be single or double stranded and may be DNA or RNA. Suitable plasmids include, for example, pZIPNeo, pLXSN and MFG.

Viruses which are conveniently used as the expression vector of the invention include viruses in which the nucleic acid of the vector is RNA, for example disabled retroviruses, and DNA viruses such as the vaccinia virus or an adenovirus. The vector or virus may be administered directly to the host, so as to achieve expression of the polypeptide in infected cells, or may first be incorporated into a cell line which is then administered to the host. When the vector or virus is administered directly to the host, the virus used is generally helper-free and replication-defective.

Preferably the expression vector comprises recombinant nucleic acid.

The present invention also provides a process for producing an expression vector other than naked nucleic acid, which process comprises cloning into a vector a gene encoding a polypeptide as defined herein. According to the process of the present invention the polypeptide-encoding gene may be cloned directly into an expression vector using known methods (Silva, Palacios, Colston and Lowrie, Microbiol Pathogenesis 12, 27–38 (1992)). The invention also provides a process for producing a cell which process comprises inserting heterologous DNA into the genome of the cell or transfecting an expression vector of the invention into a cell line. According to the present invention the heterologous DNA may be inserted into the genome using known methods (Molecular Cloning: A Laboratory Manual, T. Maniatis et al, Cold Spring Harbour, 1989).

Preferably a transfected cell line is prepared by cloning the gene encoding the polypeptide into a suitable vector, such as a retroviral shuttle vector, for example pZIPNeoSV (x), using conventional techniques and transfecting the vector into a cell line using known methods (Silva et al).

Cell lines into which expression vectors according to the present invention may be incorporated are generally mammalian and include neoplasm cell lines, MHC I and II negative cell lines, and murine and human cell lines. It is possible to use cell lines, for instance neoplasm cell lines, that originate from the host or patient to which they will be administered, particularly in order to treat established tumours. Most preferably, the cell line which is transfected is that of the neoplasm against which protection is sought.

The expression vector or cell of the invention may further include a sequence which encodes a neoplasm associated antigen or an interleukin. The expression vector or cell of the invention may include an expression vector having a sequence which encodes a neoplasm associated antigen or an interleukin. Several studies have shown that transfection of murine tumour cells with genes encoding cytokines results in the immunological rejection of the parent tumour. The cytokirne genes which have been used for this type of experiment include IL-4, IL-2, γ IFN, TNFα, IL-6, IL-7 and GM-CSF. One or more of is these genes may act synergistically with a gene encoding a polypeptide of the invention and hence maximise the chances of achieving tumour eradication.

Neoplasms caused by different and unrelated neoplasm cell lines may have common neoplasm associated antigens, in which case immunisation according to the invention with one cell line which expresses such a common antigen may give protection against other neoplasms which also have common antigens (but is unlikely to give much protection- against those neoplasms which do not). Accordingly, the present invention also provides a cell line which expresses a polypeptide as defined herein and a neoplasm associated antigen. Such cell lines may be transfected with an expression vector according to the invention together with a separate vector encoding a neoplasm associated antigen or they may be transfected with an expression vector of the invention which also includes a sequence which encodes a neoplasm associated antigen in expressible form.

According to the present invention, the expression vector or cell line may be used for the prophylaxis of neoplasms in a healthy host (patient) and for the therapeutic treatment of existing neoplasms in a host (patient). The expression vector may be administered directly to the patient. When the expression vector is a Virus, cell transfection may be carried out in vivo, by administering the virus directly to the host. Alternatively, in vitro immunisation may be carried out by exposing suitable lymphocytes removed from the host (patient) to a transfected cell line of the invention and returning the lymphocytes to the host (patient).

The present invention also provides (a) a method of treatment of neoplasms which comprises administering to the host an effective non-toxic amount of the expression vector or cell line, (b) the expression vector or cell line for use in the treatment of neoplasms and (c) the use of the expression vector or cell line for the manufacture of a medicament for the treatment neoplasms.

The present invention further provides the use of nucleic acid as defined herein for the manufacture of a medicament for the treatment of neoplasms.

The present invention provides an expression vector or cell as defined herein in purified form. The invention further provides an expression vector or cell as defined herein when isolated. The present invention further provides an expression vector as defined herein consisting essentially of nucleic acid including at least one sequence which encodes in expressible form a polypeptide which is a heat shock polypeptide (hsp) or a chaperone.

The expression vector or cells according to the invention may be administered to mammals including humans by any route appropriate to the condition to be treated, suitable routes including oral, rectal, nasal, topical (including buccal and sublingual), vaginal and parenteral (including subcutaneous, intramuscular, intravenous, intradermal, intrathecal and epidural). It will be appreciated that the preferred route may vary with, for example, the condition of the recipient and the type of treatment envisaged. Thus, existing neoplasms may be treated systematically or by a route selected to deliver the vector or cells directly to the site of the lesion. Prophylactic treatment will be aimed at stimu- lating protective immunity in tissues likely to be affected by the target neoplasms.

The expression vector of the invention may be adminis- tered to the patient alone or in combination with liposomes or other delivery molecules. The effective dosage rate depends on whether a delivery molecule is used but is generally from 100 to 500 mg vector per gram of tumour, preferably injected locally into the tumour, or 10 to 100 mg per kilogram body weight per week injected intravenously to treat or prevent metastasis.

The active ingredient in the following formulations is a vector or cell according to the invention as defined above or an in vitro immunised cell.

For each of the above-indicated utilities and indications the amount required of the individual active ingredients will depend upon a number of factors including the severity of the condition to be treated and the identity of the recipient and will ultimately be at the discretion of the attendant physician. In general, however, for each of these utilities and indications, when therapy is to be carried out with trans- fected tumour cells, a suitable, effective dose will be in the range $10^4$ to $10^{10}$ cells per kilogram body weight of recipient per week, preferably in the range $10^5$ to $10^8$ cells per kilogram body weight per week and most preferably in the range $10^5$ to $10^7$ cells per kilogram body weight per week. The dose may, if desired, by presented as two, three, four or more sub-doses administered at appropriate intervals throughout the week. When therapy is carried out with a vector containing the hsp65 gene, the effective dose will be in the range $10^4$ to $10^{12}$ helper-free, replication-defective virus per kg body weight per week, preferably in the range $10^5$ to $10^{11}$ virus per kg body weight per week and most preferably in the range $10^6$ to $10^{10}$ virus per kg body weight per week. The dosage rates stated herein are applicable to each of the dosage rates stated above.

While it is possible for the compounds to be administered alone it is preferable to present them as pharmaceutical formulations. The formulations of the present invention comprise at least one active-ingredient, as above defined, together with one or more acceptable carriers thereof and optionally other therapeutic ingredients. The carrier(s) must be "acceptable" in the sense of being compatible with the other ingredients of the formulation and not deleterious to the recipients thereof, for example, liposomes. Suitable liposomes include, for example, those comprising the posi- tively charged lipid N[1-(2,3-dioleyloxy)propyl]-N,N,N- triethylammonium (DOTMA), those comprising dio- leoylphosphatidylethanolamine (DOPE), and those comprising 3β[N-(N',N'-dimethylaminoethane)-carbamoyl] cholesterol (DC-Chol).

The formulations include those suitable for oral, rectal, nasal, topical (including buccal and sublingual), vaginal or parenteral (including subcutaneous, intramuscular, intravenous, intradermal, intrathecal and epidural) adminis- tration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a-non- aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrate (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide desired release profile.

The formulations may be applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostatis and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Injection solutions and suspensions may be prepared extemporaneously from sterile powders, granules and tablets of the kind previously described.

Preferred unit dosage formulations are those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

Examples of neoplasms which can be treated by the expression vector or cell of the invention are, for instance, sarcomas, including osteogenic and soft tissue sarcomas, carcinomas; e.g., breast-, lung-, bladder-, thyroid-, prostate-, colon-, rectum-, pancreas-, stomach-, liver-, uterine-, and ovarian carcinoma, lymphomas, including Hodgkin and non-Hodgkin lymphomas, neuroblastoma, melanoma, myeloma, Wilms tumor, and leukemias, including acute lymphoblastic leukaemia and acute myeloblastic leukaemia, gliomas and retinoblastomas.

BRIEF DESCRIPTION OF THE DRAWINGS

FIGS. 1($a$-1)-1($a$-3) show the expression of *Mycobacterium leprae* 65 kD heat shock protein (hsp) encoding gene in control and transfected cells prepared according to the invention. FIGS. 1($b$-10)-1($b$-6) show the growth of parent cells, parent cells transfected with vector alone and parent cells transfected with *Mycobacterium leprae* 65 kd hsp gene over 21 days.

FIGS. 2($a$) and 2($b$) show the in vitro cytotoxicity of splenocytes of mice immunised according to the invention. Target cells were J774-hsp 65 (□), J774 (Δ), Pu518 (◇) and Wehi 164 (○).

FIGS. 3($a$)-3($d$) show number of proliferating cells against DNA content. Results are shown for J774 cells, J774 cells transfected with vector alone, J774 cells transfected with hsp-65 gene by calcium phosphate precipitation and J774 cells transfected with hsp-65 gene by liposome mediated gene transfer.

The invention is illustrated by means of the following examples.

EXAMPLE 1

The effect of transfecting a tumour cell line with a gene which encodes for a heat shock polypeptide (hsp) was investigated by transfecting the murine macrophage tumour cell line J774 with: the *Mycobacterium leprae* 65 kD hsp-encoding gene.

Figure 1:
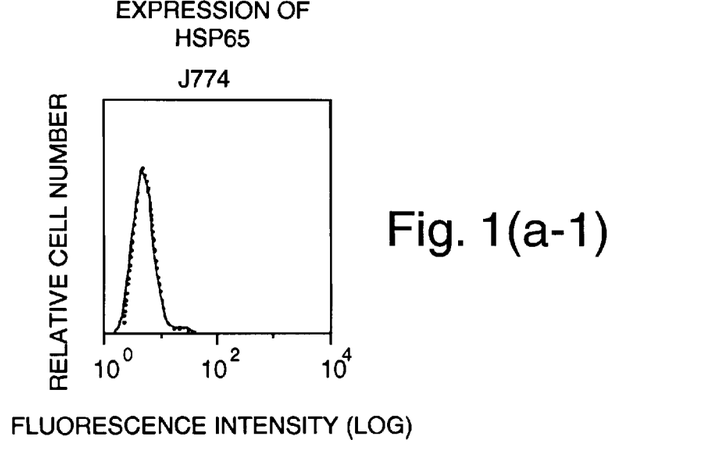

The gene transfection was carried out as described in Silva, Palacios, Colston & Lowrie, Microbiol Pathogenesis 12, 27–38 (1992). The *M.leprae* 65 kD hsp gene was cloned into the retroviral shuttle vector pZIPNeoSV(x), which was transfected by calcium phosphate precipitation into the virus-packaging cell line psi-CRE. Supernatants from neomycin resistant clones were incubated with J774-G8 cells in the presence of polybrene and neomycin resistant cells selected. Expression of the 65 kD hsp gene was assessed by FACS analysis of cells following indirect labelling using monoclonal antibody C1118, which recognises the *M.leprae* 65 kD protein, and fluorescein isothiocyanate labelled rabbit antimouse $F(ab')_2$. FIG. 1(*a*) shows the expression of hsp65 in control and transfected cells as assessed by indirect immunofluorescence. The broken line represents reactivity with the second antibody alone.

The tumourigenicity of the parent (J774) and transfected cell lines was tested in euthymic and athymic mice. Tumour cells were either the parent J774-G8 (J774) cells, the parent cell line transfected with vector alone (J774-vector), or the parent cell line transfected with the mycrobacterial hsp65 gene (J774-hsp65). Successful, stable transfection was further confirmed by Northern and Western blotting as described in Silva, et al. Five mice per group were injected intraperioneally with $10^6$ cells. FIG. 1(*b*) shows the growth of the cell lines in normal Balb/c and athymic Balb/c mice respectively. Tumour size was calculated by weighing the primary tumour and abdominal organs of test mice and subtracting the weight of abdominal organs of five age-matched normal controls.

It is clear from the results shown in FIG. 1 that the incidence of tumours in mice injected with J774-hsp65 cells is much lower than that in mice injected with J774 or J774-vector cells. 21 days after injection all mice injected with J774 or J774 vector cells have tumours weighing at least 8 g, whereas the mice injected with J774-hsp65 cells have either not developed tumours, or have tumours weighing less than 3 g.

EXAMPLE 2

Normal Balb/c, Balb/c athymic and CBA mice were injected intraperioneally with the number of tumour cells indicated in Table 1. The cells were first resuspended in 0.5 ml endotoxin free PBS. Tumour cells were prepared in the same way as in Example 1 and were either the parent cell line (J774), the parent cell line transfected with the mycobacterial hsp65 gene (J774-hsp65), or the parent cell line transfected with the vector alone (J774-vector). Tumour incidence was determined by autopsy and histological examination 21 days after injection of tumour cells. Results are shown in Table 1.

TABLE 1

The tumourigenicity of transfected and parent reticulum sarcoma cells in Balb/c, Balb/c athymic and CBA mice

| | | Tumour incidence | | |
|---|---|---|---|---|
| Injected Tumour Cells | | Balb/c | Balb/c (athymic) | CBA |
| J774 | $10^5$ | 4/5 | — | — |
| | $10^6$ | 9/10 | 5/5 | 0/10 |
| | $10^7$ | 5/5 | — | — |
| J774-vector | $10^5$ | 3/5 | — | — |
| | $10^6$ | 14/15 | 5/5 | — |
| J774-hsp65 | $10^6$ | 0/10 | 0/10 | 0/10 |
| | $10^7$ | 1/10 | — | — |
| | $5 \times 10^7$ | 0/5 | — | — |

EXAMPLE 3

J774-hsp65 cells were prepared according to the method described in Example 1. Normal and athymic Balb/c mice were immunised with four intraperitoneal injections of $10^6$ J774-hsp65 cells given at weekly intervals. On day 28 the mice were challenged intraperitoneally with $10^6$ reticulum sarcoma cells; of differing origins. Tumour incidence and tumour size were recorded 21 days after challenge. Tumour size was determined in the same way as in Example 1. Results are given in Table 2.

TABLE 2

The effect of immunisation with transfected tumour cells (J774-hsp65) on subsequent challenge with reticulum sarcoma cells

| | | Tumour Incidence | | Tumour Size (g) | |
|---|---|---|---|---|---|
| Immunisation | Challenge | Balb/c (normal) | Balb/c (athymic) | Balb/c (normal) | Balb/c (athymic) |
| J774-hsp65 | J774 | 0/10 | 5/5 | 0.28 ± 0.24(p < 0.001) | 9.99 ± 0.79 |
| None | J774 | 9/10 | 5/5 | 10.20 ± 1.18 | 10.28 ± 0.33 |
| J774-hsp65 | J774-vector | 0/15 | 5/5 | 0.68 ± 0.40(p < 0.001) | 9.81 ± 1.09 |
| None | J774-vector | 10/10 | 5/5 | 10.93 ± 0.35 | 9.92 ± 0.38 |
| J774-hsp65 | Pu518 | 2/10 | 5/5 | 3.33 ± 1.06(p < 0.001) | 8.09 ± 0.57 |
| None | Pu518 | 5/5 | 4/4 | 9.96 ± 0.50 | 7.69 ± 0.58 |
| J774-hsp65 | Wehi 164 | 7/9 | 5/5 | 7.74 ± 1.12 | 7.14 ± 1.94 |
| None | Wehi 164 | 5/5 | 4/4 | 8.80 ± 0.68 | 7.87 ± 0.58 |

The results given in Table 2 show that normal Balb/c mice, when injected with J774-hsp cells, develop good immunity against J774 and J774-vector cells. The results also show that normal Balb/c immunised mice have some resistance to the Pu518 cell line; not all mice developed tumours and in those which did, the tumours which formed were of significantly smaller size than in non-immunised mice. Resistance of immunised mice against the Wehi 164 cell line was poor; a large proportion of mice developed tumours which were similar size to the tumours which developed in non-immunised mice.

Immunisation with J774-hsp65 cells had no effect on Balb/c athymic mice.

EXAMPLE 4

J774-hsp65 cells were prepared according to the method described in Example 1.

Figure 2A:
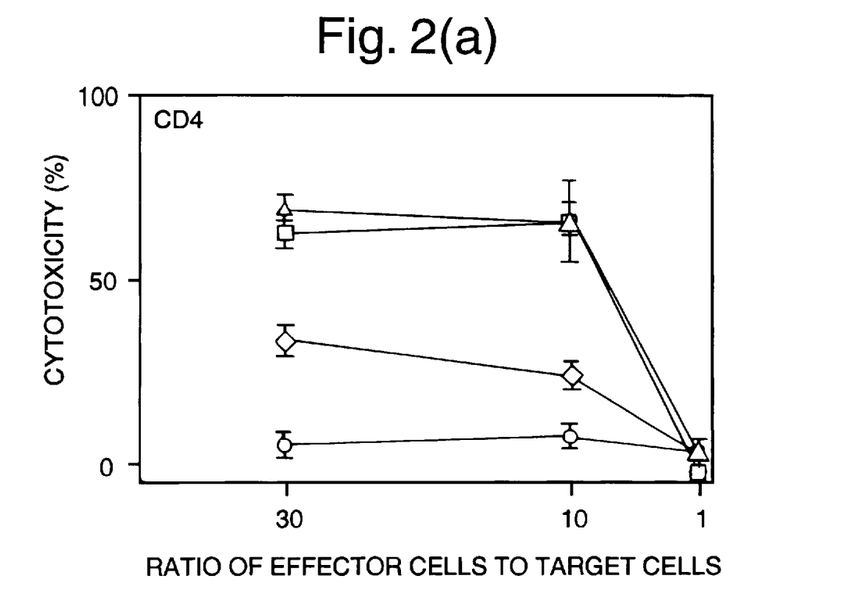
Figure 2B:
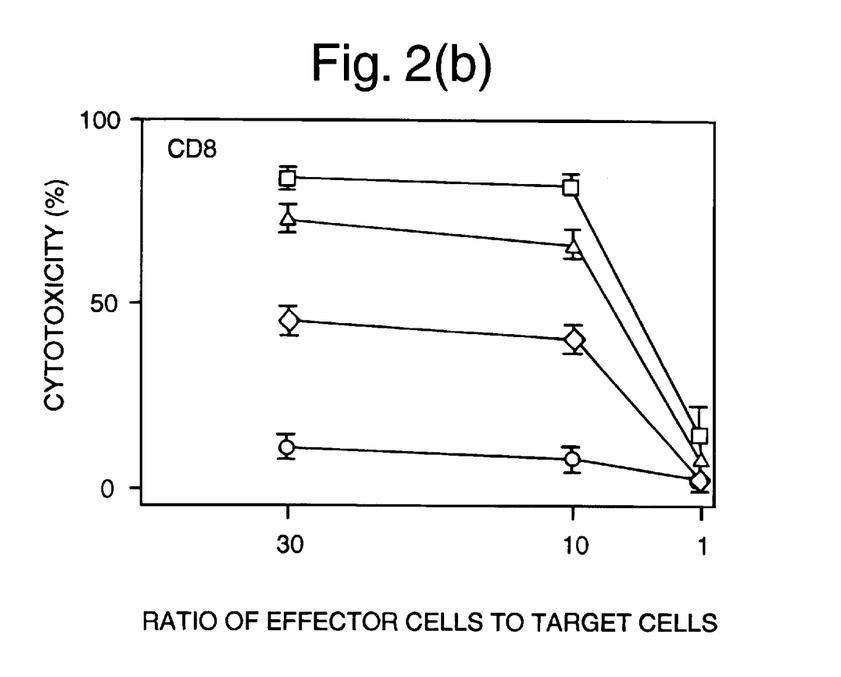
Figure 3A:
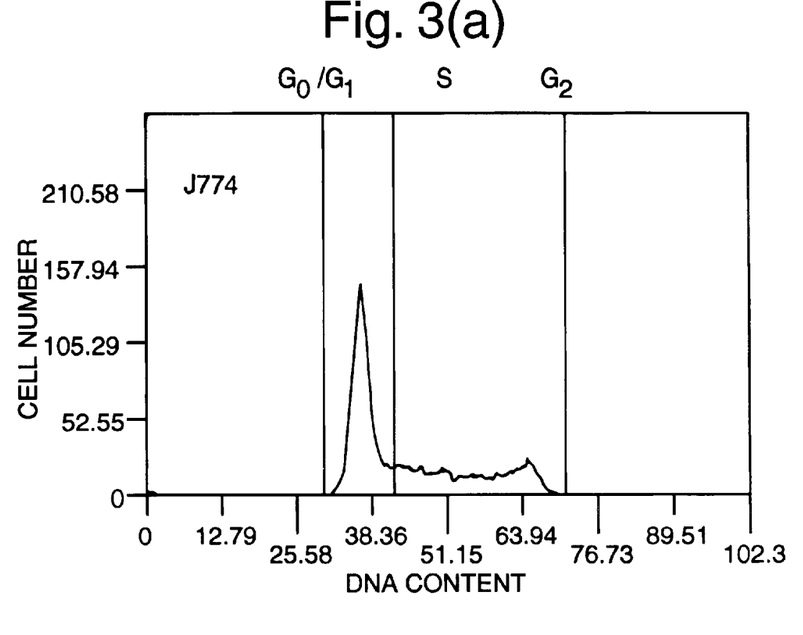
Figure 3B:
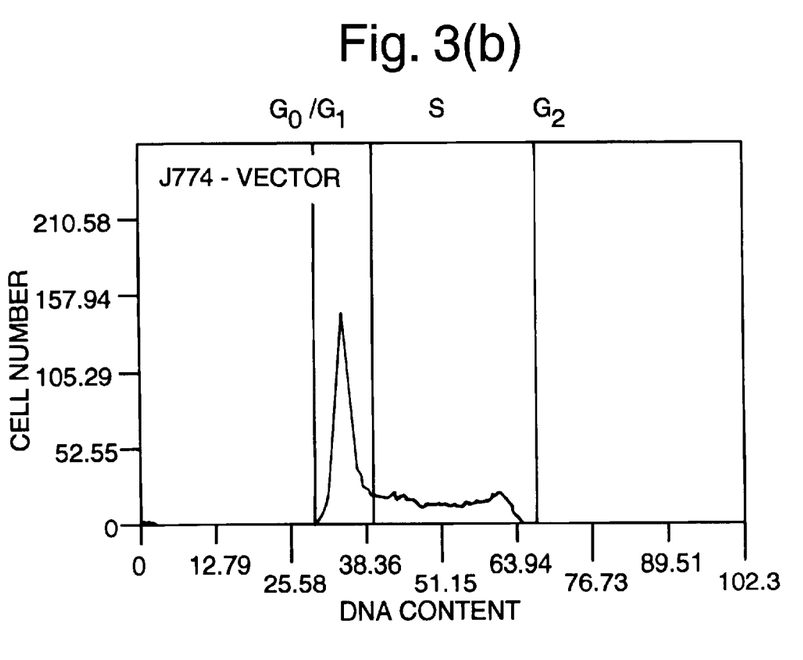
Figure 3C:
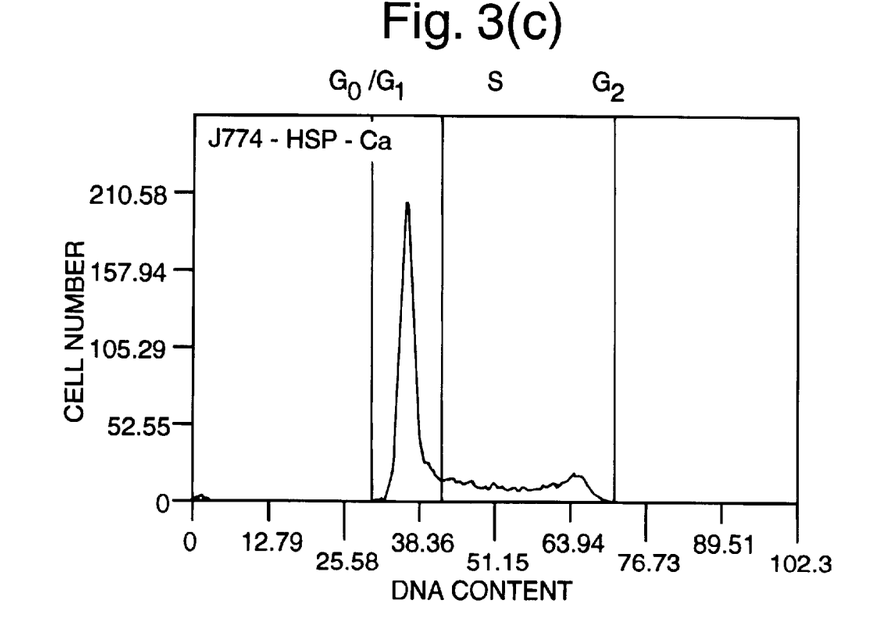
Figure 3D:
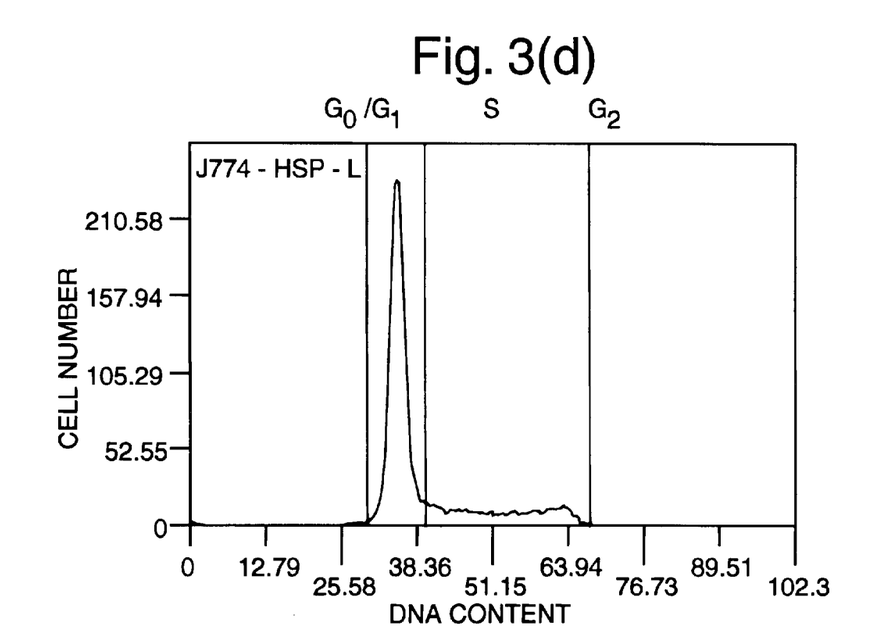

The in vitro cytotoxic activity of splenocytes from mice immunised with J774-hsp65 cells was investigated by immunising normal Balb/c and Balb/c athymic mice with four intraperitoneal injections of $10^6$ J774-hsp65 cells at weekly intervals. On day 28, spleens were removed and single cell suspensions prepared in RPMI 1640 plus 10% foetal calf serum. The cells were incubated for 6 days with J774-hsp65 cells irradiated by 30 Gy. B cells were removed by panning on rabbit anti-mouse IgG-coated plates. CD4 and CD8 T cell subsets were purified using the method described in Lukacs and Kurlander, J. Immunol. 143, 3731–3736 (1989). NK and CD4 or CD8 cells were removed by treatment of $10^7$/ml cells with 10 µg/ml PK136 (anti-NK1.1) and anti-L3T4 or anti-Lyt 2 monoclonal antibodies at 4° C. for 30 min, followed by incubation with 1/10 dilution of rabbit complement at 37° C. for 60 min, resulting in CD4 and CD8 populations which were over 90% pure as determined by FACS analysis. Cytotoxic activity was measured by incubating varying number of CD4 or CD8 effector cells with 2000/well target cells labelled with $^{51}$Cr in triplicate wells for 6 h at 37° C. in a v-bottomed 96-well microtiter plate. $^{51}$Cr release was measured in wells containing effector T cells and target cells ($cpm_{experimental}$), wells containing target cells incubated in medium alone ($cpm_{spontaneous}$) and in wells containing target cells plus 0.1% Triton X ($cpm_{maximal}$). Cytotoxicity was calculated using the formula:

$$\% \text{ cytotoxicity} = \frac{(cpm_{experimental}) - (cpm_{spontaneous})}{(cpm_{maximal}) - (cpm_{spontaneous})} \times 100$$

The results are shown in FIG. 2 as the mean±standard deviation. Target cells were J774-hsp65 (□), J774 (Δ), Pu518 (◇) and Wehi 164 (○).

The results in FIG. 2 show that in vitro cytotoxicity of splenocytes from immunised mice is as great against J774-hsp65 as against J774 cells and much greater than against Pu 518 cells (cytotoxicity was significant but less) and Wehi 164 cells (no cytotoxicity).

EXAMPLE 5

The effect of hsp-transfection on the cell cycle of tumour cells was examined by staining the cells with a DNA-specific benzimide dye, Hoechst 33342. J774 tumour cells transfected with the *Mycobacterium leprae* hsp-65 gene by two different methods, Ca-phosphate precipitation (J774-HSP-Ca) and liposome mediated gene transfer (J774-HSP-L), as well as untransfected and vector-transfected control J774 cells ($2 \times 10^6$/ml) were stained with 10 µg/ml Hoechst dye for 30 min. at 37° C. Using FACS analyser, DNA histograms were obtained, and the percentage of cells in each phase of the cell cycle was determined.

Results in FIG. 3 show that the number of proliferating cells with high DNA content (S and G2 phases) decreased in tumour cells transfected with the hsp-65 gene (J774-HSP-Ca and J774-HSP-L). Simultaneously, an increase has been found in the number of hsp65 expressing cells with low DNA content (G0/G1 phases) compared to the control tumour cells. These experiments indicate that transfection of tumour cells with hsp-65 gene results in a change in the cell cycle control, and suggest that one of the basic characteristics of tumour cells, uncontrolled proliferation, is altered.

EXAMPLE 6

Mutations in the p53 gene resulting in dysfunctional p53 tumour suppressor protein is the most frequently observed genetic lesion in malignant tumours. Tumour cells transfected with *Mycobacterium leprae* hsp65 and control tumour cells were examined for the expression of p53 tumour suppressor protein. J774-HSP cells were prepared according to the method described in Example 1. Expression of p53 protein was assessed by FACS analysis. Cell membranes were permeabilized by 0.05% saponin, then the cells were incubated with monoclonal antibodies specific for p53 (Ab-248 and Ab-421, provided by D. Lane) and FITC-labelled rabbit antimouse F(ab')2 second antibody.

Figure 4:
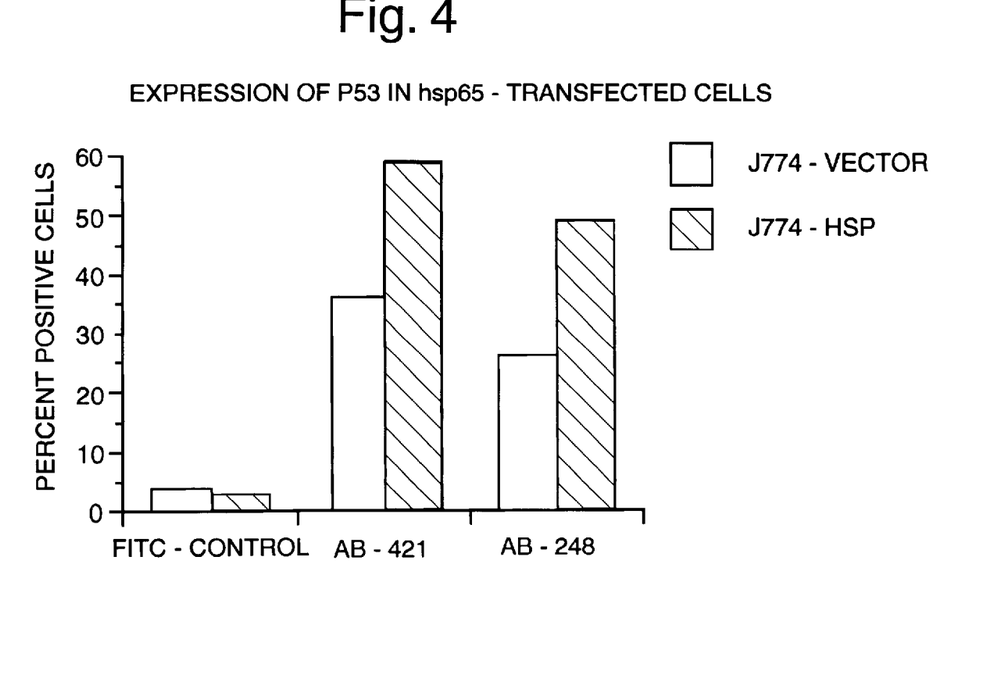
FIG. 4 shows percentage of cells expressing p53 epitopes in J774-hsp 65 cells.

FIG. 4 shows increased expression of both p53 epitopes in J774-hsp65 cells. Since p53 is a DNA-binding protein essential for normal cell cycle control, our experiments suggest that hsp65 may exert its effect on the cell cycle through p53 tumour suppressor protein. The increased chaperone activity of the hsp65 transfected cells could result in the proper folding and conformation of the ineffective, mutant p53 protein, thereby correcting its loss of tumour suppressor function.

EXAMPLE 7

Balb/c mice with advanced histiocytic sarcomas received in vivo gene therapy with the *Mycobacterium leprae* hsp65 gene fourteen days after tumour induction with $10^6$ J774 tumour cells. A mixture of 100 µg pZIPML65 plasmid and 100 µg liposome was injected four times intraperitoneally into the tumour and intravenously to treat metastatic cells. On day 21 mice were sacrificed, autopsy performed and tumour sizes were determined.

Figure 5:
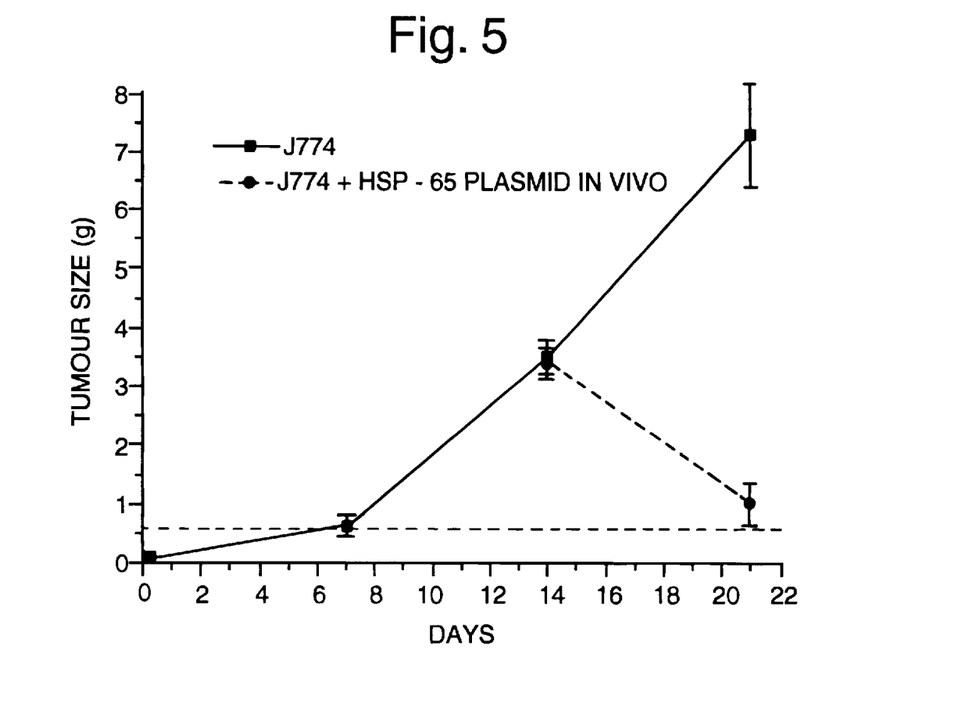
FIG. 5 shows tumour size in mice receiving plasmid containing the hsp 65 gene (○) and in mice not receiving the hsp 65 gene (□).

Results in FIG. 5 show tumour regression in mice receiving plasmid containing the hsp65 gene. Only one tumour was found in the group of six treated mice, while all six untreated controls developed large tumours by day 21. Although further studies are needed and histological evidence obtained for tumour regression, our data indicate that the hsp65 gene can be successfully delivered in vivo into tumours resulting in tumour regression. In vivo injection of the hsp65 gene can result in lost tumorigenicity of those cells which become transfected while the cytotoxic T cell response generated by the transfected cells could complete the eradication of remaining untransfected cells. This duel effect makes hsp65 an attractive choice in the gene therapy of cancers.

What is claimed is:

1. A method of inhibiting the growth of a tumor in a human or other mammal which comprises directly administering to said tumor an effective non-toxic amount of an expression vector, said expression vector including at least one sequence in expressible form which encodes a bacterial heat shock polypeptide (hsp) whereby the growth of said tumor is inhibited.

2. The method of claim 1 in which the said expression vector is a virus.

3. The method of claim 2, wherein the virus is vaccinia virus.

4. The method of claim 2, wherein the virus is an adenovirus.

5. The method of claim 1, wherein the expression vector comprises RNA.

6. The method of claim 1, wherein the expression vector is a replication incompetent retrovirus.

7. The method of claim 1, wherein the expression vector is a retroviral shuttle vector.

8. The method of claim 7, wherein the expression vector is pZIPNeoSV(x).

9. The method of claim 1, wherein the expression vector is a plasmid.

10. The method of claim 1, wherein the expression vector is an episomal vector.

11. The method of claim 1, wherein the heat shock polypeptide is a mycobacterial hsp.

12. The method of claim 11, wherein the heat shock polypeptide is selected from the group consisting of *M. tuberculosis* 65 kDa antigen, *M. leprae* 65 kD hsp and *M. leprae* 70 kD hsp.

13. The method of claim 1 further comprising directly administering to said tumor an expression vector having a sequence which encodes a tumor associated antigen or an interleukin.

14. A method of inhibiting the growth of a tumor in a human or other mammal which comprises directly administering to said tumor an effective non-toxic amount of an expression vector, said expression vector including at least one sequence in expressible form which encodes a mycobacterial 65 kD heat shock polypeptide, whereby the growth of said tumor is inhibited.

15. The method of claim 14, wherein the expression vector further comprises a pharmaceutically acceptable carrier which is a liposome.

* * * * *